United States Patent
Tran et al.

(10) Patent No.: US 8,128,693 B2
(45) Date of Patent: Mar. 6, 2012

(54) INTRAOCULAR LENS SYSTEM

(75) Inventors: Son Trung Tran, Arlington, TX (US); David L. Jinkerson, Benbrook, TX (US)

(73) Assignee: Novartis AG, Basel (CH)

( * ) Notice: Subject to any disclaimer, the term of this patent is extended or adjusted under 35 U.S.C. 154(b) by 1281 days.

(21) Appl. No.: 11/196,984

(22) Filed: Aug. 4, 2005

(65) Prior Publication Data
US 2005/0273163 A1 Dec. 8, 2005

Related U.S. Application Data

(63) Continuation of application No. 10/753,239, filed on Jan. 8, 2004, now Pat. No. 6,972,034, which is a continuation-in-part of application No. 10/618,954, filed on Jul. 14, 2003, now Pat. No. 6,960,231.

(51) Int. Cl.
*A61F 2/16* (2006.01)

(52) U.S. Cl. .................................................. 623/6.41

(58) Field of Classification Search .............. 623/6.16, 623/6.17, 6.4, 6.6
See application file for complete search history.

(56) References Cited

U.S. PATENT DOCUMENTS

| | | | |
|---|---|---|---|
| 4,073,014 A | 2/1978 | Poler | |
| 4,122,556 A | 10/1978 | Poler | |
| 4,575,373 A | 3/1986 | Johnson | |
| 4,661,108 A | 4/1987 | Grendahl et al. | |
| 4,731,078 A * | 3/1988 | Stoy et al. | 623/6.13 |
| 4,919,151 A | 4/1990 | Grubbs et al. | |
| 5,026,783 A | 6/1991 | Grubbs et al. | |
| 5,222,981 A | 6/1993 | Werblin | |
| 5,358,520 A | 10/1994 | Patel | |
| 5,480,426 A | 1/1996 | Chu | |
| 5,549,668 A | 8/1996 | O'Donnell, Jr. | |
| 5,571,177 A | 11/1996 | Deacon et al. | |
| 5,628,798 A | 5/1997 | Eggleston et al. | |
| 5,800,533 A | 9/1998 | Eggleston et al. | |
| 5,814,103 A | 9/1998 | Lipshitz et al. | |
| 6,015,842 A | 1/2000 | LeBoeuf et al. | |
| 6,406,494 B1 | 6/2002 | Laguette et al. | |
| 6,464,725 B2 | 10/2002 | Skotton | |
| 6,797,004 B1 | 9/2004 | Brady et al. | |
| 2001/0034552 A1 | 10/2001 | Young et al. | |
| 2002/0173846 A1 | 11/2002 | Blake et al. | |
| 2003/0158560 A1 | 8/2003 | Portney | |
| 2003/0187504 A1 | 10/2003 | Weinschenk, III et al. | |

FOREIGN PATENT DOCUMENTS

| | | | |
|---|---|---|---|
| EP | 1138282 A1 * | 10/2001 | |
| WO | WO 01/87189 A2 | 11/2001 | |

* cited by examiner

*Primary Examiner* — William H. Matthews
(74) *Attorney, Agent, or Firm* — Darien Reddick

(57) ABSTRACT

A two part lens system. The first part is a ring-like supporting component that is implanted in the capsular bag following cataract surgery. The first component is a non-optical component and contains a pair of haptics for fixating the first component within the capsular bag. The second component is an optical component that contains all of the corrective optical power of the lens system. The second component has a pair of tabs for locking the second component within the first component.

22 Claims, 5 Drawing Sheets

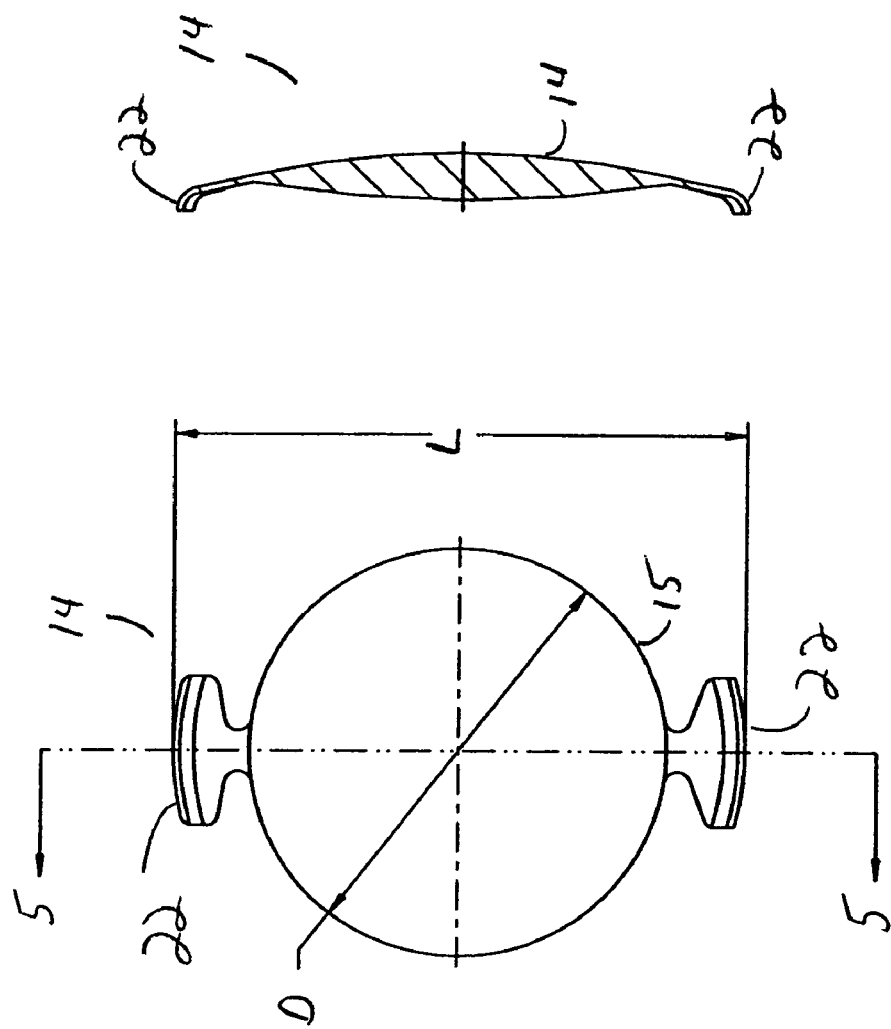

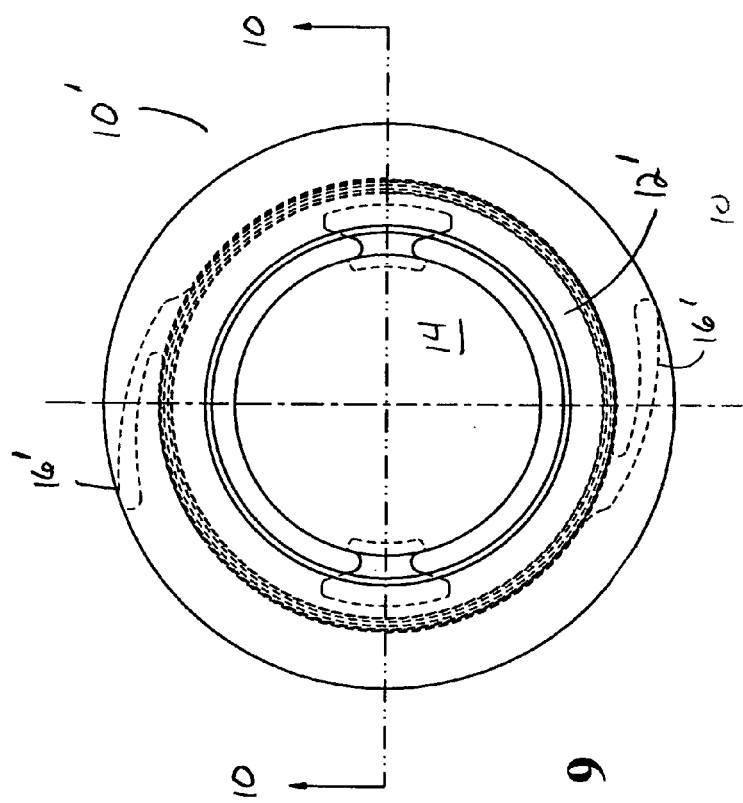
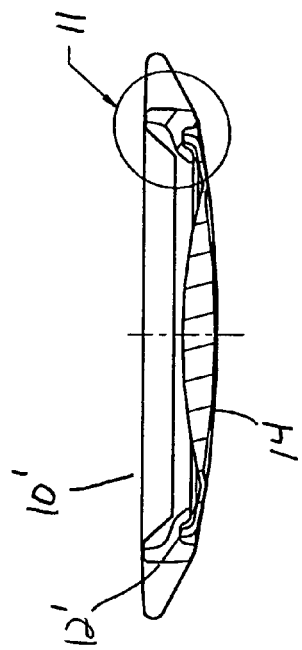
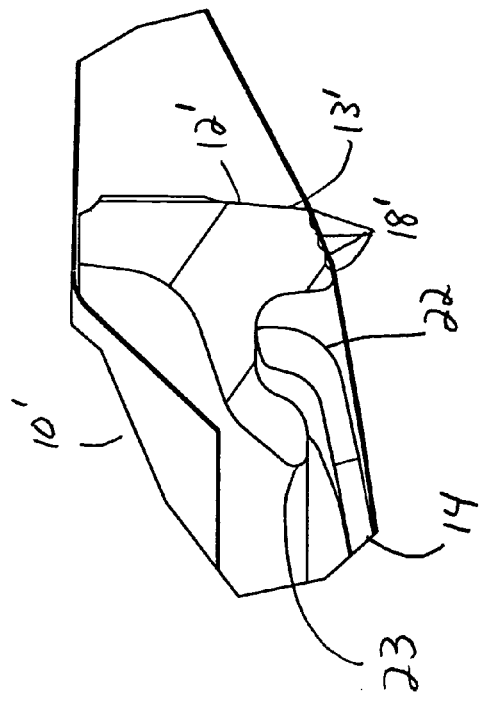
FIG. 9
FIG. 10
FIG. 11

INTRAOCULAR LENS SYSTEM

This application is a continuation of U.S. patent application Ser. No. 10/753,239, filed Jan. 8, 2004 (now U.S. Pat. No. 6,972,034), which is a continuation-in-part of U.S. patent application Ser. No. 10/618,954, filed Jul. 14, 2003 (now U.S. Pat. No. 6,960,231).

BACKGROUND OF THE INVENTION

This invention relates generally to the field of intraocular lenses (IOL) and, more particularly, to multi-lens IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Prior to the present invention, when a cataract or other disease required the removal of the natural lens and replacement with an artificial IOL, the IOL was a monofocal lens. Most IOLs are sold in power increments of +/−0.5 diopters, and the ultimate power of the lens depends upon where the lens sits along the optical axis. The fixed increment of the lens, and the slight variation in lens placement can result in less than optimum vision. Although this situation occurs relatively infrequently, and generally is not severe, some patients ultimately are required to use a pair of spectacles or contact lenses for optimum vision. If the power of the implanted lens is incorrect, removal and exchange of a new lens is difficult because of fibrosis of the lens haptics within the capsular bag.

There have been several prior suggested adjustable power IOLs, none of which have been commercially introduced. For example, U.S. Pat. No. 5,222,981 (Werblin) and U.S. Pat. No. 5,358,520 (Patel), the entire contents of which being incorporated herein by reference, suggest the use of a second or even a third optic that may be implanted and attached to a previously implanted primary optic so as to adjust the overall optic power of the multi-lens system. U.S. Pat. Nos. 5,628,798 and 5,800,533 (Eggleston, et al.), the entire contents of which being incorporated herein by reference, disclose a threadedly adjustable IOL wherein the location of the optic along the visual axis may be adjusted. U.S. Pat. No. 4,575,373 (Johnson), the entire contents of which being incorporated herein by reference, discloses an IOL having an optic and an outer ring and connections between the optic and the outer ring made from a heat-shrinkable plastic. The connections are heated with a laser to adjust the power of the IOL. U.S. Pat. Nos. 4,919,151 and 5,026,783 (Grubbs, et al.), the entire contents of which being incorporated herein by reference, disclose a lens made from a polymer that swells or otherwise changes shape. The lens is implanted or injected into the capsule bag and selectively polymerized so as to adjust the power of the optic. U.S. Pat. No. 5,571,177 (Deacon, et al.), the entire contents of which being incorporated herein by reference, discloses an IOL having haptics with frangible stiffeners. Once implanted in an eye, the stiffeners are selectively cut or heated above their $t_g$ by laser radiation, causing the stiffness of the haptic to change and adjusting the location of the lens within the capsule bag. The multi-lens designs and the threadedly adjustable designs are not optimized for the reduction or elimination of posterior capsule opacification (PCO).

Therefore, a need continues to exist for a safe and stable intraocular lens system that provides adjustment of lens power. Such a lens system could be used in cararact or clear lens exchange surgeries.

BRIEF SUMMARY OF THE INVENTION

The present invention improves upon the prior art by providing a two part lens system. The first part is a ring-like supporting component that is implanted in the capsular bag following cataract surgery. The first component is a non-optical component and contains a pair of haptics for fixating the first component within the capsular bag. The second component is an optical component that contains all of the corrective optical power of the lens system. The second component has a pair of tabs for locking the second component within the first component.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible adjustable lens system.

Still another objective of the present invention is to provide a safe and biocompatible lens system that can be implanted through a small incision.

Still another objective of the present invention is to provide a safe and biocompatible lens system that helps reduce the incidence of PCO.

Still another objective of the present invention is to provide a safe and biocompatible lens system for use in cataract and/or clear lens exchange surgeries.

These and other advantages and objectives of the present invention will become apparent from the detailed description and claims that follow.

BRIEF DESCRIPTION OF THE DRAWING

FIG. 4 is an enlarged plan view of the second component of the lens system of the present system.

FIG. 5 is an enlarged cross-sectional view of the second component of the lens system of the present system taken at line 5-5 in FIG. 4.

FIG. 9 is an enlarged plan view of the second embodiment of the assembled lens system of the present system.

FIG. 10 is an enlarged cross-sectional view of the second embodiment of the assembled lens system of the present system taken at line 10-10 in FIG. 9.

FIG. 11 is an enlarged partial cross-sectional view of the second embodiment of the lens system of the present system taken at circle 11 in FIG. 10.

DETAILED DESCRIPTION OF THE INVENTION

Figure 1:
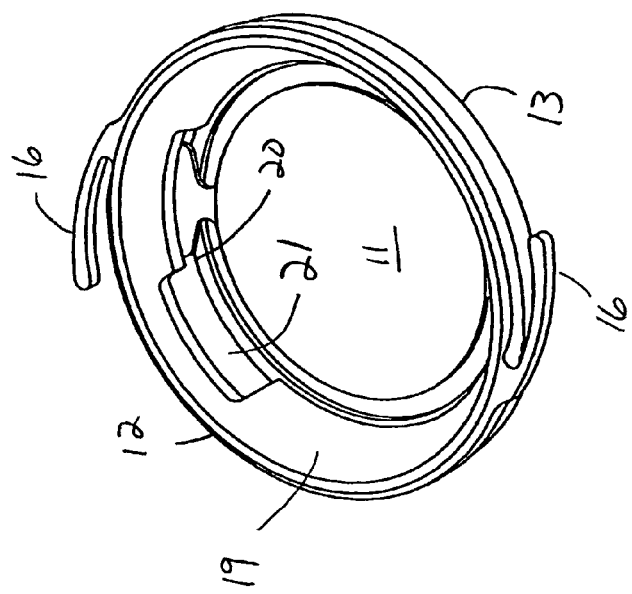
FIG. 1 is an enlarged perspective view of the first embodiment of the assembled lens system of the present system.
Figure 3:
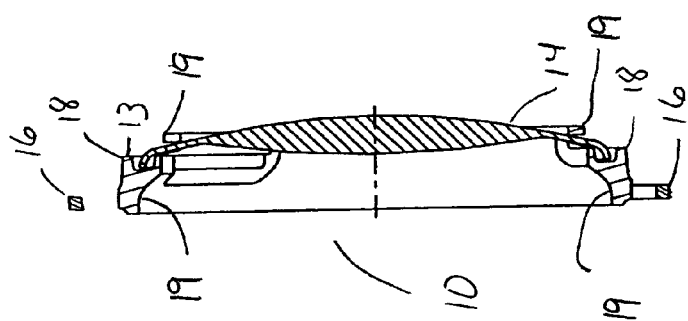
FIG. 3 is an enlarged cross-sectional view of the first embodiment of the assembled lens system of the present system taken at line 3-3 in FIG. 2.
Figure 2:
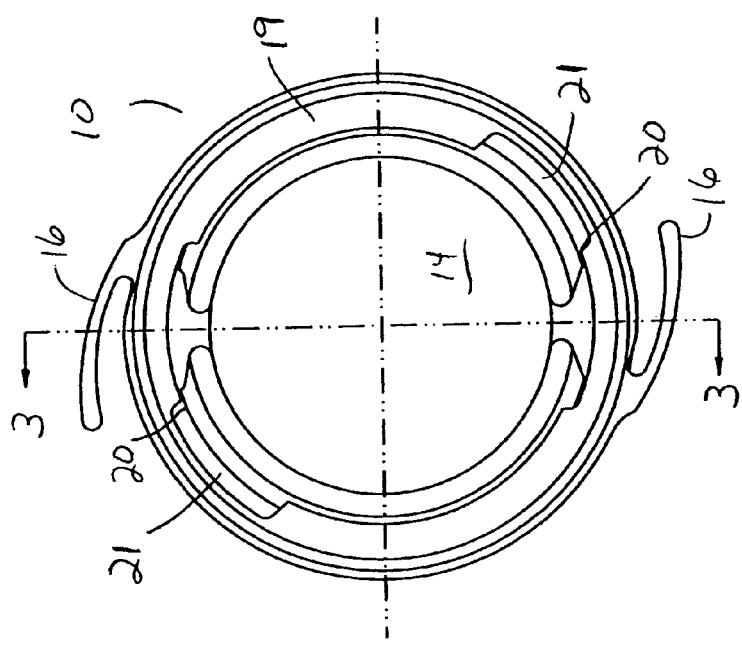
FIG. 2 is an enlarged plan view of the first embodiment of the assembled lens system of the present system.

As best seen in FIGS. 1-3, lens system 10 of the present invention generally consists of first, or base, component 12 and second, or optical, component 14. Base component 12 is generally ring-like, having hollow center 11 and contains a plurality of integrally formed haptics 16 and is preferably formed in any suitable overall diameter, for example, between approximately 10.0 millimeters and 12.0 millimeters, a suitable interior diameter, for example, between approximately 7.0 millimeters and 9.0 millimeters and made from a soft, foldable material such as a soft acrylic. Alternatively, base component 12 may be made from a material that is stiffer relative to optical component 14 or less stiff relative to optical component 14. By way of example, component 12 may be made of rubber elastomers, such as butyl rubber, latex rubber, natural rubber, pure gum rubber, neoprene rubber, acrylonitrile rubber, styrene-butadiene rubber, ethylene-propylene diene monomer rubber, acrylonitrile-butadiene-styrene (ABS) rubber, epichlorohydrin rubber, hypalon rubber, silicone rubber and siloxane elastomers, such as poly(dimethylsiloxane), polyurethane rubber, viton rubber, ethylene-butylene rubber, isobutylene rubber and elastomers of polyphosphazenes, like poly(bis-trifluorethoxyphosphazene) oly(dimethylphosphazene) and poly(phenylmethylphosphazene). Preferably, base component 12 is constructed so as to allow it to be compressed and inserted into an eye through an incision of approximately 2.0 mm. Base component 12 may also be formed so as to be opaque, such as by frosting or texturing the anterior and/or posterior surfaces of base component 12. Base component 12 may also contain a chromophore to block ultraviolet and/or blue and/or green light, such chromophore(s) being well-known in the art. As best seen in FIG. 3, posterior surface 13 of base component 12 preferably has a plurality of posterior circumferential rings or bands 18 that present a sharp, square edge against the posterior capsule, such sharp edges being widely believed to help inhibit PCO. Interior surface 19 of base component 12 contains locking slot 20 into which optical component 14 fits in the manner described below.

As best seen in FIGS. 4-5, optical component 14 is generally circular with an optic 15 having diameter D, for example, between approximately 4.0 millimeters and 7.0 millimeters. Optical component 14 tapers from being relatively thick in the middle to having a relatively thin, or sharp, edge that contains a plurality of tabs 22 integrally formed with optic 15 so as to give optical component 14 overall length L between approximately 7.5 millimeters and 8.5 millimeters and preferably, is made from a soft, foldable material such as a soft acrylic. Lens component 14 may also contain a chromophore to block ultraviolet and/or blue light, such chromophore(s) being well-known in the art, but unlike base component 12, lens component 14 is optically clear.

As best seen in FIGS. 2 and 3, lens system 10 is assembled by placing tabs 22 of lens component 14 in wide portions 21 of slots 20 and rotating lens component 14 slightly clockwise so as to lock tabs 22 within slots 20. In such an assembly, optical component 14 does not compress and vault during contraction of the capsular bag, because tabs 22 can slide inward and outward within slots 20 during compression of haptic 16 and base component 12. Such a construction makes lens component 14 very axially stable.

Figure 8:
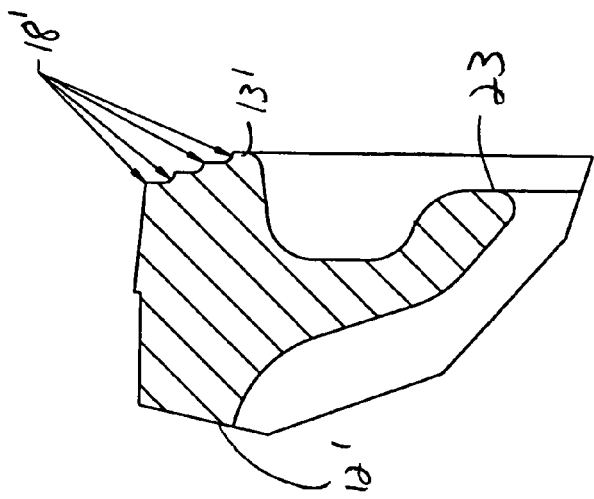
FIG. 8 is an enlarged partial cross-sectional view of the second component of the lens system of the present system taken at circle 8 in FIG. 7.
Figure 7:
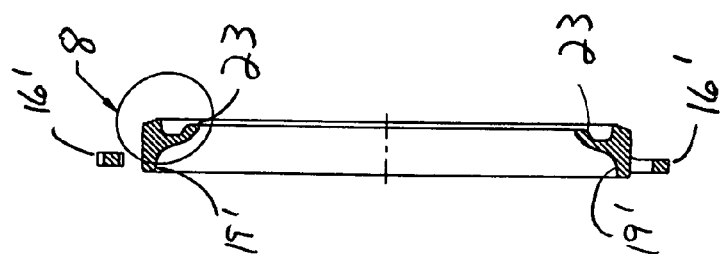
FIG. 7 is an enlarged cross-sectional view of the second embodiment of the first component of the lens system of the present system taken at line 7-7 in FIG. 6.
Figure 6:
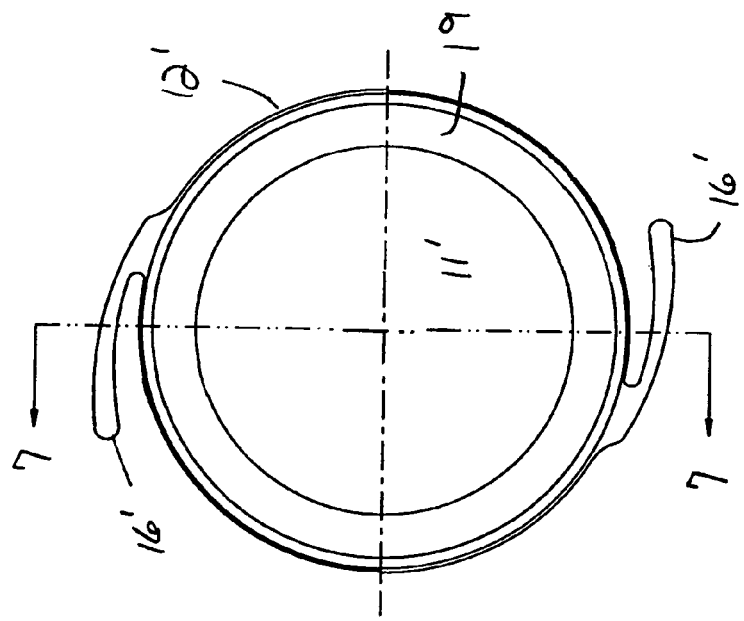
FIG. 6 is an enlarged plan view of the second embodiment of the first component of the lens system of the present system.

In a second embodiment of the present invention, best seen in FIGS. 6-11, lens system 10' of the present invention generally consists of first, or base, component 12' and second, or optical, component 14. Base component 12' is generally ring-like, having hollow center 11' and contains a plurality of integrally formed haptics 16' and is otherwise constructed in a manner similar to base component 12. As best seen in FIG. 8, posterior surface 13' of base component 12' preferably has a plurality of posterior circumferential rings or bands 18' that present a sharp, square edge against the posterior capsule, such sharp edges being widely believed to help inhibit PCO. Interior surface 19' of base component 12' is smooth and contains lip 23 into which optical component 14 fits in the manner described below.

As best seen in FIGS. 9-11, lens system 10' is assembled by placing tabs 22 of lens component 14 under lip 23. In such an assembly, optical component 14 does not compress and vault during contraction of the capsular bag, because tabs 22 can slide inward and outward on lip 23 during compression of haptic 16' and base component 12'. Such a construction makes lens component 14 very axially stable. Another advantage of such a construction is that no rotation of component 14 is necessary, allowing component to be implanted more easily and in any rotational position. Being able freely to locate component 14 rotationally can be an advantage, particularly with toric components 14.

Figure 13:
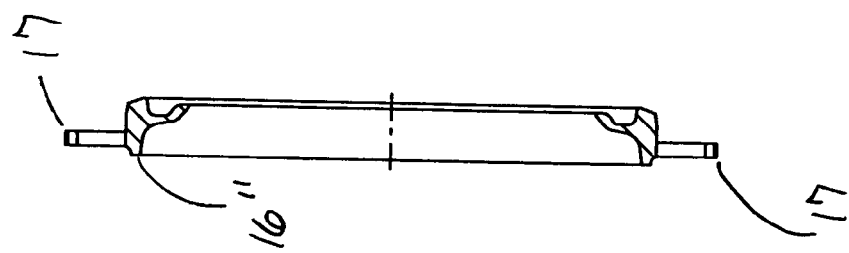
FIG. 13 is an enlarged cross-sectional view of the third embodiment of the first component of the lens system of the present system taken at line 13-13 in FIG. 12.
Figure 12:
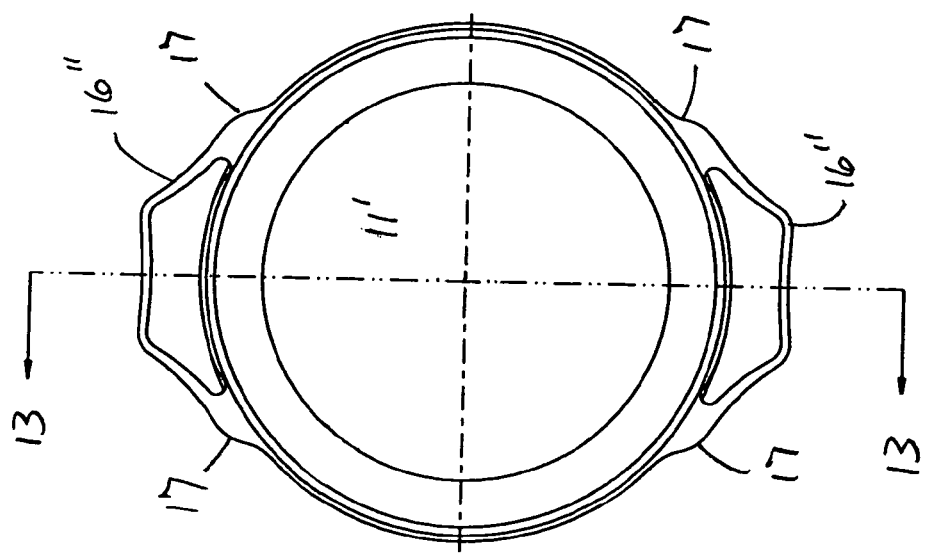
FIG. 12 is an enlarged plan view of the third embodiment of the first component of the lens system of the present system.

In a third embodiment of the present invention, best seen in FIGS. 12 and 13, component 12" generally ring-like, and generally of a construction similar to component 12 and 12' except that component 12" contains a plurality of integrally formed haptics 16" that are of a closed-loop design and connected to component 12" on both ends 17.

This description is given for purposes of illustration and explanation. It will be apparent to those skilled in the relevant art that changes and modifications may be made to the invention described above without departing from its scope or spirit.

We claim:

1. An intraocular lens system, comprising:
   a) a ring-shaped base component comprising:
      a first end; and
      a hollow center defining an interior surface, the hollow center extending through the entire thickness of the base component, the interior surface defining a circumferential lip defining a circumferential groove extending axially from the first end; and
   b) an optical component having a plurality of integrally formed tabs, the tabs sized and spaced to fit under the lip in the base component in any rotational position and to secure the optical component relative to the base component, the secured tabs radially slideable within the groove to prevent compression and vaulting of the optical component during compression of the ring-shaped base component during contraction of the capsular bag.

2. The lens system of claim 1 wherein the base component is opaque.

3. The lens system of claim 1 wherein the base component is stiff relative to the optical component.

4. The lens system of claim 1 wherein the base component is flexible relative to the optical component.

5. The lens system of claim 1 wherein the base component is made from a rubber elastomer.

6. The lens system of claim 1 wherein the base component contains a chromophore to block ultraviolet and/or blue and/or green light.

7. The lens system of claim 4 wherein the base component is made from a soft acrylic.

8. The lens system of claim 4 wherein the base component is made from butyl rubber, latex rubber, natural rubber, pure gum rubber, neoprene rubber, acrylonitrile rubber, styrene-butadiene rubber, ethylene-propylene diene monomer rubber, acrylonitrile-butadiene- styrene (ABS) rubber, epichlorohydrin rubber, hypalon rubber, silicone rubber and siloxane elastomers, such as poly(dimethylsiloxane), polyurethane rubber, viton rubber, ethylene-butylene rubber, isobutylene rubber and elastomers of polyphosphazenes, like poly(bistrifluorethoxyphosphazene) oly(dimethylphosphazene) or poly(phenylmethylphosphazene).

9. The lens system of claim 1 further comprising a plurality of posterior circumferential rings formed on a posterior surface of the base component.

10. The intraocular lens systemof claim 1, wherein the ring-shaped base component further comprises at least one haptic.

11. An intraocular lens system, comprising:
a) a ring-shaped base component having a first end and a hollow center, the hollow center extending through the entire thickness of the base component, the base component further comprising a circumferential lip defining a circumferential groove extending axially from the first end, the base component being opaque; and
b) an optical component having a plurality of integrally formed tabs, the optical component being soft relative to the base component and the tabs being sized and spaced to fit under the lip in the base component in any rotational position and to secure the optical component relative to the base component, the secured tabs radially slideable within the groove to prevent compression and vaulting of the optical component during compression of the ring-shaped base component during contraction of the capsular bag.

12. The lens system of claim 11 further comprising a plurality of posterior circumferential rings formed on a posterior surface of the base component.

13. An intraocular lens system comprising:
a base component comprising:
a ring-shaped member including a first end;
a central opening extending axially through the ring-shaped member;
an interior surface defined by the central opening, the interior surface defining an annular lip extending radially inwards into the central opening of the ring-shaped member, an end portion of the annular lip extending in an axial direction to define an annular groove at the first end; and
an optical component coupled to the base component, the optical component comprising:
an optical portion; and
a plurality of integrally formed tabs extending from the optical portion adapted to be retained within the annular groove in any rotational position of the optical element relative to the base component, the plurality of integrally formed tabs radially slideable within the groove relative to the base component to prevent compression and vaulting of the optical component during compression of the base component during contraction of the capsular bag.

14. The lens system of claim 13, wherein the base component is opaque.

15. The lens system of claim 13, wherein the base component is stiff relative to the optical component.

16. The lens system of claim 13, wherein the base component is flexible relative to the optical component.

17. The lens system of claim 16, wherein the base component is formed from a rubber elastomer.

18. The lens system of claim 16, wherein the base component is formed from butyl rubber, latex rubber, natural rubber, pure gum rubber, neoprene rubber, acrylonitrile rubber, styrene-butadiene rubber, ethylene-propylene diene monomer rubber, acrylonitrile-butadiene- styrene (ABS) rubber, epichlorohydrin rubber, hypalon rubber, silicone rubber and siloxane elastomers, such as poly(dimethylsiloxane), polyurethane rubber, viton rubber, ethylene-butylene rubber, isobutylene rubber and elastomers of polyphosphazenes, like poly(bistrifluorethoxyphosphazene) oly(dimethylphosphazene), or poly(phenylmethylphosphazene).

19. The system of claim 13 further comprising a plurality of circumferential rings formed on a posterior surface of the base component.

20. The lens system of claim 13, wherein the base component contains a chromophore to block ultraviolet and/or blue and/or green light.

21. The lens system of claim 16, wherein the base component is made from a soft acrylic.

22. The lens system of claim 13, wherein the annular groove defines an outer circumferential rim and an inner circumferential rim and wherein the inner circumferential rim is axially offset from the outer circumferential rim.

* * * * *